US006262303B1

(12) United States Patent
De Santis et al.

(10) Patent No.: US 6,262,303 B1
(45) Date of Patent: Jul. 17, 2001

(54) PROCESS FOR THE PREPARATION OF S-N,N'-BIS[2-HYDROXY-1-(HYDROXYMETHYL)ETHYL]-5-[(2-HYDROXY-1-OXOPROPYL)-AMINO]-2,4,6-TRIIODO-1,3-BENZENEDICARBOXAMIDE

(75) Inventors: Nicola De Santis; Salvatore Incandela, both of Milan (IT)

(73) Assignee: Dibra S.p.A., Milan (IT)

( * ) Notice: Subject to any disclaimer, the term of this patent is extended or adjusted under 35 U.S.C. 154(b) by 0 days.

(21) Appl. No.: 09/302,352

(22) Filed: Apr. 30, 1999

Related U.S. Application Data

(60) Provisional application No. 60/084,735, filed on May 8, 1998.

(51) Int. Cl.[7] ............... C07C 233/00; C07C 231/02
(52) U.S. Cl. ............... 564/153; 424/9.452; 564/142
(58) Field of Search ............... 564/153, 142; 424/9.452

(56) References Cited

U.S. PATENT DOCUMENTS 4,001,323    1/1977   Felder et al. .
5,204,086 *  4/1993   Willie ........................... 564/153
5,817,861   10/1998   Villa et al. .
5,847,212 * 12/1998   Wang et al. ................... 564/153
5,948,940 *  9/1999   Sorensen et al. .............. 564/153

FOREIGN PATENT DOCUMENTS 2 272 218   11/1994  (GB) .
1 472 050    4/1997  (GB) .

* cited by examiner

*Primary Examiner*—Shailendra Kumar
(74) *Attorney, Agent, or Firm*—Nixon & Vanderhye

(57) ABSTRACT

A process for the preparation of S-N,N'-bis[2-hydroxy-1-(hydroxymethyl)ethyl]-5-[(2-hydroxy-1-oxopropyl)amino]-2,4,6-triiodo-1,3-benzenedicarboxamide, comprising the formation of S-N,N'-bis[2-hydro-xy-1-(hydroxymethyl)ethyl]-5-[(2-(acetyloxy)-1-oxopro-pyl)amino]-2,4,6-triiodo-1,3-benzenedicarboxamide star-ting from S-(−)-5-[[2-(acetyloxy)-1-oxopropyl]amino]-2,4,6-triiodo-1,3-benzenedicarboxylic acid dichloride and 2-amino-1,3-propanediol in a solvent, characterized in that the solvent is selected from the group consisting of: lower alcohols, monoalkyl ether glycols and straight or branched cyclic alkyl ethers.

11 Claims, No Drawings

PROCESS FOR THE PREPARATION OF S-N,N'-BIS[2-HYDROXY-1-(HYDROXYMETHYL)ETHYL]-5-[(2-HYDROXY-1-OXOPROPYL)-AMINO]-2,4,6-TRIIODO-1,3-BENZENEDICARBOXAMIDE

This application claims priority of Ser. No. 60/084,735 the disclosure of which is hereby incorporated by reference.

The present invention relates to a process for the preparation of S-N,N'-bis[2-hydroxy-1-(hydroxymethyl)ethyl]-5-[(2-hydroxy-1-oxo-propyl)amino]-2,4,6-triio-do-1,3-benzenedicarboxamide of formula (I), more commonly known as Iopamidol, one of the most widely marketed iodinated contrast, comprising a novel step for the synthesis of the intermediate S-N,N'-bis[2-hydro-xy-1-(hydroxymethyl)ethyl]-5-[(2-(acetyloxy)-1-oxopropyl)amino]-2,4,6-triiodo-1,3-benzenedicarboxamide of formula (II).

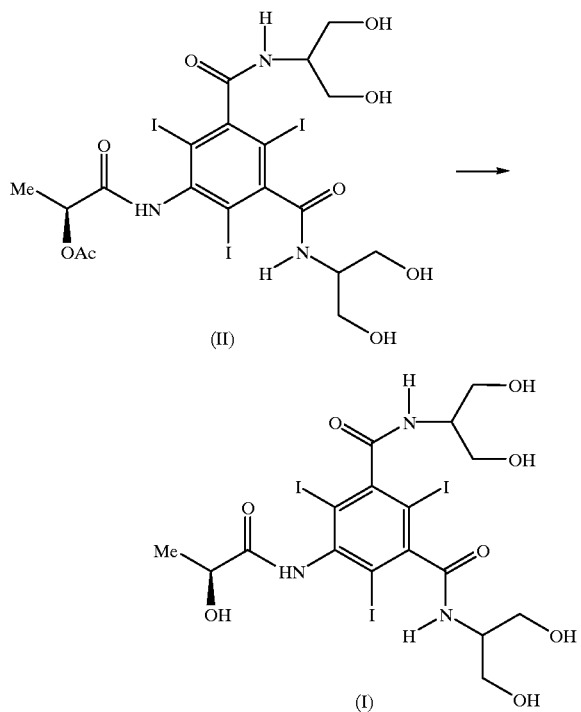

The synthesis of Iopamidol was first described in GB 1,472,050 and it involves the steps represented in the following Scheme:

Scheme

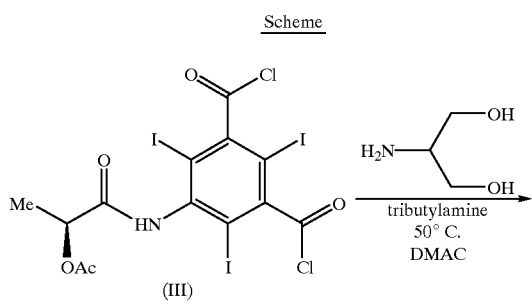

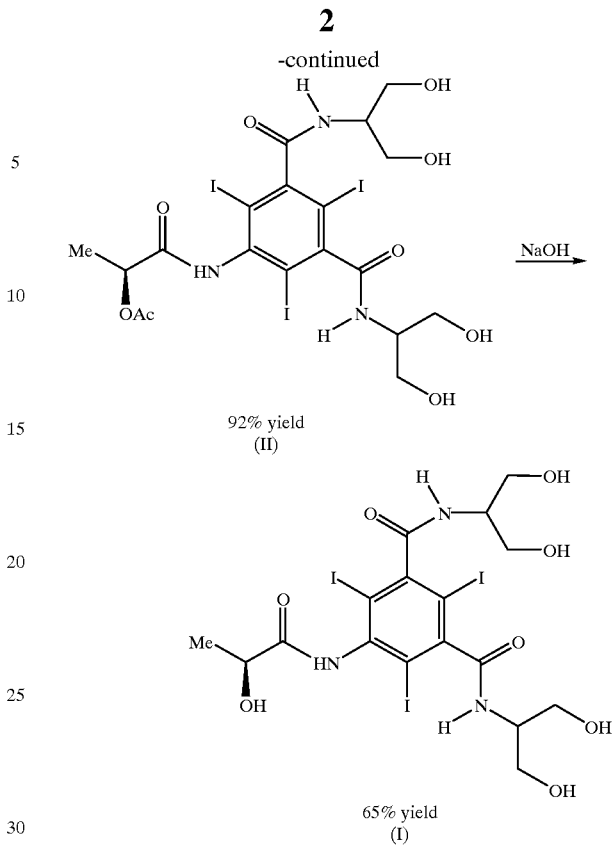

and precisely the reaction of S-(−)-5-[[2-(acetyloxy)-1-oxopropyl]amino]-2,4,6-triiodo-1,3-benzenedicarboxylic acid dichloride of formula (III) dissolved in dimethylacetamide (DMAC) with a slight excess of 2-amino-1,3-propanediol (commonly named serinol) also dissolved in dimethylacetamide, in the presence of tributylamine, to give compound (II), S-N,N'-bis[2-hy-droxy-1-(hydroxymethyl)ethyl]-5-[(2-(acetyloxy)-1-oxopropyl)amino]-2,4,6-triiodo-1,3-benzenedicarboxamide.

The ratio between compound (II), serinol and tributylamine is 1:2.5:2 expressed in equivalents. The reaction is carried out at 50° C., yielding, after some hours, the desired product in a 92% yield.

The work up of the reaction mixture, described in the cited Patent, comprises evaporating dimethylacetamide, suspending the oily residue in methylene chloride, repeatedly taking up the precipitate with hot methylene chloride.

The resulting residue is then hydrolysed to Iopamidol with NaOH, the subsequent treatment of the resulting solution with a cationic and an anionic resin allows to purify it from the salts before recrystallizing from ethyl alcohol.

The main problems with this process are the following:
- the distillation of the solvent under vacuum at the end of the reaction is a quite troublesome operation from the industrial point of view, DMAC being a high boiling product (165° C.);
- the use of DMAC gives rise to N-[2-hydroxy-1-(hydroxymethyl)ethyl]-N'-dimethyl-5-[(2-hydroxy-oxo-propyl)amino]-2,4,6-triiodo-1,3-benzenedicarboxamide, (hereinafter referred to as impurity I).

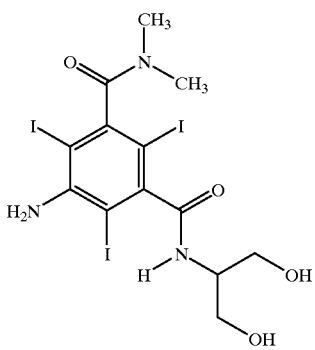

impurity I one of the seven impurities of Iopamidol described in Pharmeuropa, vol. 6, no.4, December 1994, pages 343–345, which is ascribable essentially to the production of dimethylamine by DMAC during the work up of the reaction;

moreover, the use of such a high boiling solvent is quite troublesome and difficult so that solvent traces remain in the recovered solid product, which traces, however, have not to exceed 650 ppm (USP limit for Iopamidol).

A first attempt to replace DMAC was made by GB 2,272,218 (priority 27.10.1992), in which the preparation of only compound (II) is described, using solvents different from DMAC, i.e. acetone or lower ($C_1$–$C_4$) alcohols, in the presence of a base, preferably tributylamine.

As acknowledged by the inventors themselves in the subsequently published patent application GB 2,311,524, which will be discussed in the following, Iopamidol obtained from intermediate (II), in spite of his having an acceptable purity grade, also had different impurities instead of the impurity I.

Physicians and the authorities which grant drug marketing authorizations, require drugs with very low levels of impurities in order to minimize any involved risks of side-effects or toxic effects for the patient.

As far as iodinated contrast agents are concerned, such a requirement is due to the total amount of administered product, which is much higher than that of other medicaments. By way of example, the injected dose of contrast agent can reach and even exceed 150 g.

Iopamidol has, in fact, recently undergone a change in its pharmacopoeia requirements, (Italian Pharmacopoeia IX, 3rd revision 1994; US Pharmacopoeia XXIII, 5th revision, Nov. 15, 1996) and it has now to contain at most 0.25% of impurities.

The recently published British patent application GB 2,311,524 (priority 29.03.1996), discloses an alternative approach to obtain Iopamidol with such purity characteristics.

GB 2,311,524 describes the preparation of compound (I), using N-methylpyrrolidone as reaction solvent, in the presence of a base, preferably selected from serinol, tributylamine, triethylamine or an inorganic carbonate, claiming a higher purity of the obtained compound (II), which is reflected in the final purity of Iopamidol.

The preferred process involves the reaction of compound (III) with serinol in N-methylpyrrolidone, in the presence of previously purified triethylamine or of sodium carbonate. The subsequent treatment of the resulting crude through a battery of ion exchange resins (strong cationic, weak anionic, strong anionic, weak anionic, as described in GB 2,287,024) yields the final compound Iopamidol, with a declared purity in accordance with the revisioned pharmacopoeia requirements.

It is therefore evident from the study of the prior art the impelling exigency of:

avoiding the presence of DMAC, thereby also improving the profile of the impurities present in Iopamidol as well as the carrying out of the industrial process;

easily removing the reaction solvent: N-methylpyrrolidone belongs, in fact, to the same class of dipolar aprotic solvent as DMAC and, having a similar high boiling point, is therefore difficult to remove completely.

We have now surprisingly found that Iopamidol fulfilling the pharmacopoeia requirements can be prepared by the process of the invention comprising:

a novel method for the preparation of compound (II);

the easy transformation of the resulting compound (II) into Iopamidol without involving basic hydrolysis neither complex chromatographic treatments.

It is therefore the object of the present invention the preparation of compound (I) comprising the formation of compound (II) by reacting compound (III) with only serinol in a solvent selected from a lower alcohol and monoalkyl ether glycols of the class of alkylcellosolves and cyclic, straight or branched alkyl ethers.

"Lower alcohol" means a straight or branched $C_2$–$C_5$ alcohol, preferably a secondary alcohol. Particularly preferred are t-butanol and sec-butanol.

Glycols are preferably comprised from $C_3$ and $C_7$, ethoxyethanol and methoxyethanol being particularly preferred.

Cyclic, straight or branched alkyl ethers are $C_4$–$C_{10}$, and they are preferably selected from the group consisting of: dioxane, diglyme and methyl tert-butyl ether.

We have surprisingly found that the reaction carried out without the addition of a base, in particular tributylamine as in the prior art, and in an alcoholic or ether solvent, allows to effectively overcome the above mentioned problems related to the presence of DMAC, at the same time providing a final product with the purity characteristics in accordance with, or even better than, the present pharmacopoeia requirements.

As already discussed in GB patent application 2,311,524 (as well as described in WO 9214539) it was already known in the prior art that the reaction can be carried out without the use of a base, using more than 4 equivalents of serinol, which thus acts as an acceptor of the hydrochloric acid formed during the reaction itself. The reaction is, however, carried out in DMAC, thus involving the problems mentioned above.

GB 2,311,524 itself envisages the possible use of a serinol excess as a base (see Example 1, serinol/compound (II) molar ratio=4.36:1), but the solvent is anyway N-methylpyrrolidone and in all the described examples the reaction is carried out under nitrogen atmosphere, which is not a condition easy to reproduce industrially, and the subsequent hydrolysis process to Iopamidol involves a troublesome step through different ion exchange columns.

We have surprisingly found that when serinol is added in a molar ratio to compound (III) ranging from 6 to 25, preferably from 8 to 15, the addition of a base for the subsequent hydrolysis of compound (II) to Iopamidol is no longer necessary.

The reaction temperature can range from −10° C. to 100° C., preferably from 48 to 85° C., in this last range the reaction time being surprisingly reduced to 1–6 h.

At the end of the reaction between serinol and compound (III), checked by HPLC analysis, the solvent is distilled off to dryness at a temperature from 40 to 100° C., under a pressure of 10–20 mbar, thus completing the reaction. After that, the acetate group is hydrolysed by addition of water, preferably in amounts of 2 to 4 kg of water per mole of compound (III), being the solution already basic due to the presence of the serinol excess.

Then the solution is brought to 50–70° C., preferably 55–65° C., keeping said temperature for a time from 4 to 8 h, preferably from 5 to 7 h. Finally the solution is neutralized by addition of HCl.

Operating according to the process of the present invention, the final reaction mixture contains, in addition to compound (I), only serinol, serinol hydrochloride and serinol acetate.

In this way, the only present cation is serinol, thereby improving the desalting process as well as the Iopamidol purification.

The absence in the final solution of dipolar aprotic solvents, which are, on the contrary, always present in the prior art, allows to carry out the purification of compound (I) without using rather expensive industrial equipments, such as the nanofiltration unit for the preliminary desalting and removal of DMAC (see WO 9214539) or the column battery mentioned above for N-methylpyrrolidone (see GB 2,311,524).

The process of the invention includes a chromatographic purification on a conventional column comprising a solid phase selected from the group consisting of macroporous highly cross-linked styrene resins, preferably Amberlite(R) XAD 1600, 1600 T and 16 (Rohm & Haas) or equivalents marketed by other manufacturers.

Elution is carried out with water, washing until disappearance of the compound, checked by UV analysis.

After concentration of the aqueous phase, desalting is performed by means of a battery (in series or in mixed bed) consisting of a strong cationic resin of sulfonic type, regenerated in the acidic form, and a mean anionic resin of the secondary amine type, regenerated in the OH⁻ form.

The preferred cationic resins are selected from the group consisting of: Dowex C 350, Amberjet 1200, Amberlite IR 120. The preferred anionic resin is Relite MG 1.

The desalted solution is concentrated and purified by crystallization from a suitable solvent, as already known in literature (GB 1,472,050, GB 2,708,601, U.S. Pat. No. 5,689,002, WO 97/02235, EP 747344).

Serinol is recovered simply by displacement from the above cationic resin with a 4% ammonia solution. The ammonia eluate is concentrated under vacuum to remove water and ammonia and then crystallized according to the procedures described in Italian patent application MI 96 A 002546.

The recovered product has such a quality as to be used in the process of the present invention (see Experimental section).

Iopamidol obtained by the process of the invention has an impurity content not higher than 0.25%, obtained by HPLC analysis, as described in the Pharmacopoeia (see above). No DMAC from previous preparation steps of compound (III), neither other residual solvents (from other synthetic steps) are detected, traces of the process solvent being present in amounts not higher than the requirements established by ICH (International Conference on Harmonization) concerning the presence of residual solvents in pharmaceuticals.

The absence of DMAC or other dipolar aprotic solvents reduces the presence of the crystallization solvent to about one third compared with the prior art, as the dipolar aprotic solvent no longer retains the solvents.

Furthermore, the use of serinol as the base, in addition to removing impurity I, also reduces the risk of formation of S-N,N'-bis[2-hydroxy-1-(hydroxymethyl)ethyl]-5-amino-2,4,6-triiodo-1,3-benzenedicarboxamide of formula (IV)

(IV)

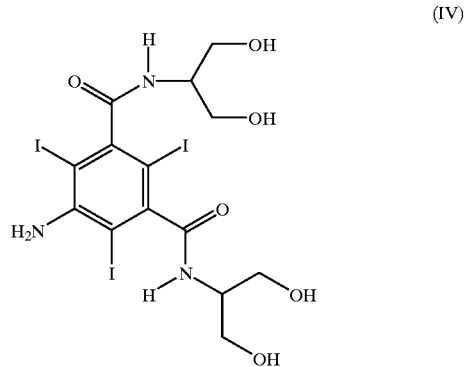

in which a free amino group is present, such compound therefore belonging to the harmful class of aromatic amines and being very difficult to separate from compound (I) once it is formed. The decrease in this by-product in the process of the invention is likely due to the lower basicity of serinol in the complementary hydrolysis reaction of the amide with lactic acid at the 5- position.

The following examples illustrate the best experimental conditions to carry out the process of the invention.

Experimental Section

EXAMPLE 1

Preparation of Iopamidol Using Sec-butanol in the Formation Reaction of Compound (II)

127.5 g (0.179 mol) of compound (III) (prepared as described in U.S. Pat. No. 5,672,735) are suspended in 593 g of sec-butanol in a reactor, under mechanical stirring. The mixture is heated to a temperature of 55° C. and added with 136 g (1.49 mol) of serinol, keeping this temperature for 3 hours. After said time, the solvent is evaporated off under reduced pressure. 400 g of water are added, heating at 55° C. for 6 hours to complete the saponification. After neutralizing with 34% HCl, the aqueous solution is eluted with water on XAD 1600 (500 mL) until disappearance of the product. The eluate is concentrated to a volume of about 1 L and the solution is then eluted on a cationic resin (Dowex C350, 1,2 L regenerated in the H⁺ form) and on an anionic resin (Relite MG 1, 1 L, regenerated in the OH⁻form).

Finally, water is evaporated off under vacuum and the residue is crystallized from sec-butanol, to obtain 128 g (0.16 mol) of the desired product.

Yield: 92%

HPLC assay: 99.88% (% area)

HPLC Method: see US Pharmacopeia XXIII, 5th revision, Nov. 15, 1996.

Residual solvent: sec-BuOH 0.009%

GC Method: in accordance with the method described in US Pharmacopeia XXIII, chapter "Organic volatile impurities" Method IV (head space).

EXAMPLE 2

Preparation of Iopamidol Using t-butanol in the Formation Reaction of Compound (II)

127.5 g (0.179 mol) of compound (III) are suspended in 593 g of t-butanol, in a reactor, under mechanical stirring.

The mixture is heated to a temperature of 20° C. and added with 136 g (1.49 mol) of serinol, keeping this temperature for 4 hours. After said time, the solvent is evaporated off under reduced pressure. 400 g of water are added, heating at 55° C. for 6 hours to complete the saponification. After neutralizing with 34% HCl, the aqueous solution is eluted with water on XAD 1600 (500 mL) until disappearance of the product. The eluate is concentrated to a volume of about 1 L and the solution is then eluted on a cationic resin (Dowex C350. 1,2 L regenerated in the H$^+$ form) and on an anionic resin (Relite MG 1, 1 L, regenerated in the OH-form).

Finally, water is evaporated off under vacuum and the residue is crystallized from sec-butanol, to obtain 104 g (0.13 mol) of the desired product.

Yield: 75%

HPLC assay: 99.75% (% area)

Residual solvent: t-BuOH 0.01%

EXAMPLE 3

Preparation of Iopamidol Using Isopropanol in the Formation Reaction of Compound (II)

127.5 g (0.179 mol) of compound (III) are suspended in 593 g isopropanol, in a reactor, under mechanical stirring. The mixture is heated to a temperature of 50° C. and added with 136 g (1.49 mol) of serinol, keeping this temperature for 4 hours. After said time, the solvent is evaporated off under reduced pressure. 400 g of water are added, heating at 55° C. for 6 hours to complete the saponification. After neutralizing with 34% HCl, the aqueous solution is eluted with water on XAD 1600 (500 mL) until disappearance of the product. The eluate is concentrated to a volume of about 1 L and the solution is then eluted on a cationic resin (Dowex C350, 1,2 L regenerated in the H$^+$ form) and on an anionic resin (Relite MG 1, 1 L, regenerated in the OH$^-$form).

Finally, water is evaporated off under vacuum and the residue is crystallized from sec-butanol, to obtain 122,4 g (0.157 mol) of the desired product.

Yield: 88%

HPLC assay: 99.82% (% area)

Residual solvent: i-PrOH 0.009%

EXAMPLE 4

Preparation of Iopamidol Using Dioxane in the Formation Reaction of Compound (II)

127.5 g (0.179 mol) of compound (III) are suspended in 593 g of dioxane, in a reactor, under mechanical stirring. The mixture is heated to a temperature of 30° C. and added with 136 g (1.49 mol) of serinol, keeping this temperature for 5 hours. After said time, the solvent is evaporated off under reduced pressure. 400 g of water are added, heating at 55° C. for 6 hours to complete the saponification. After neutralizing with 34% HCl, the aqueous solution is eluted with water on XAD 1600 (500 mL) until disappearance of the product. The eluate is concentrated to a volume of about 1 L and the solution is then eluted on a cationic resin (Dowex C350, 1,2 L regenerated in the H$^+$ form) and on an anionic resin (Relite MG 1, 1 L, regenerated in the OH$^-$ form).

Finally, water is evaporated off under vacuum and the residue is crystallized from sec-butanol, to obtain 97.4 g (0.125 mol) of the desired product.

Yield: 70%

HPLC assay: 99.77% (% area)

Residual solvent: dioxane 0.01%

EXAMPLE 5

Preparation of Iopamidol Using methyl tert-butyl ether in the Formation Reaction of Compound (II)

127.5 g (0.179 mol) of compound (III) are suspended in 593 g of methyl tert-butyl ether, in a reactor, under mechanical stirring. The mixture is heated to a temperature of 30° C. and added with 136 g (1.49 mol) of serinol, keeping this temperature for 5 hours. After said time, the solvent is evaporated off under reduced pressure. 400 g of water are added, heating at 55° C. for 6 hours to complete the saponification. After neutralizing with 34% HCl, the aqueous solution is eluted on XAD 1600 (500 mL) with water until disappearance of the product. The eluate is concentrated to a volume of about 1 L and the solution is then eluted on a cationic resin (Dowex C350. 1,2 L regenerated in the H$^+$form) and on an anionic resin (Relite MG 1, 1 L, regenerated in the OH$^-$form).

Finally, water is evaporated off under vacuum and the residue is crystallized from sec-butanol, to obtain 116.8 g (0.15 mol) of the desired product.

Yield: 84%

HPLC assay: 99.78% (% area)

Residual solvent: methyl tert-butyl ether 0.01%.

EXAMPLE 6

Preparation of Iopamidol Using 2-methoxyethanol in the Formation Reaction of Compound (II)

38.8 g (0.054 mol) of compound (III) are suspended in 180 g of 2-methoxyethanol, in a reactor, under mechanical stirring. The mixture is heated to a temperature of 55° C. and added with 41.4 g (0.45 mol) of serinol, keeping this temperature for 3 hours. After said time, the solvent is evaporated off under reduced pressure. 120 g of water are added, heating at 55° C. for 6 hours to complete the saponification. After neutralizing with 34% HCl, the aqueous solution is eluted on XAD 1600 (150 mL) with water until disappearance of the product. The eluate is concentrated to a volume of about 0.5 L and the solution is then eluted on a cationic resin (Dowex C350. 0.4 L, regenerated in the H$^+$form ) and on an anionic resin (Relite MG 1, 0.33 L, regenerated in the OH$^-$form).

Finally, water is evaporated under vacuum and the residue is crystallized from 2-methoxyethanol, to obtain 37.3 g (0.048 mol) of the desired product.

Yield: 89%

HPLC assay: 99.8% (% area)

Residual solvent: 2-methoxyethanol 0.0045%

EXAMPLE 7

Preparation of Iopamidol Using 2-ethoxyethanol in the Formation Reaction of Compound (II)

38.8 g (0.054 mol) of compound (III) are suspended in 180 g of 2-ethoxyethanol, in a reactor, under mechanical stirring. The mixture is heated to a temperature of 55° C. and added with 41.4 g (0.45 mol) of serinol, keeping this temperature for 3 hours. After said time, the solvent is evaporated off under reduced pressure. 120 g of water are added, heating at 55° C. for 6 hours to complete the saponification. After neutralizing with 34% HCl, the aqueous solution is eluted on XAD 1600 (150 mL) with water until disappearance of the product. The eluate is concentrated to a volume of about 0.5 L and the solution is then eluted on a cationic resin (Dowex C350. 0.4 L, regenerated in the H⁺ form ) and on an anionic resin (Relite MG 1, 0.33 L, regenerated in the OH⁻form).

Finally, water is evaporated under vacuum and the residue is crystallized from 2-methoxyethanol, to obtain 38.2 g (0.049 mol) of the desired product.

Yield: 91%

HPLC assay: 99.83% (% area)

Residual solvent: 2-ethoxyethanol 0.009%

EXAMPLE 8

Recovery of Serinol Used in Example 1

After eluting the solution of the product obtained as described in Example 1, on the resin (Dowex C350. 1,2 L, regenerated in the H⁺form ), serinol is displaced with 750 g of a 4% by weight ammonia solution, subsequently washing with deionized water to neutral pH. The resulting solution is concentrated under 12 mm Hg at a temperature of 50–60° C. to remove ammonia, until obtaining a residue containing about 5–10% of residual water. 250 g of dry 2-butanol are loaded, cooling to 5° C. for 3 hours.

The mixture is then filtered and dried at 30° C. under nitrogen stream to obtain 85 g of serinol of good quality, which can be recycled in the synthesis of Iopamidol (GC Assay: 99.9%, method described by F. Uggeri et al., Journal of Chromatography, 432, 1988).

What is claimed is:

1. A process for the preparation of S-N,N'-bis[2-hydroxy-1-(hydroxymethyl)ethyl]-5-[(2-hydroxy-1-oxopropyl)amino]-2,4,6-triiodo-1,3-benzenedicarboxamide, said process comprising forming S-N,N'-bis[2-hydroxy-1-(hydroxymethyl)ethyl]-5-[(2-acetyloxy-1-oxopropyl)amino]-2,4,6-triiodo-1,3-benzenedicarboxamide from S-(−)-5-[[2-(acetyloxy)-1-oxopropyl]-amino]-2,4,6-triiodo-1,3-benzendicarboxylic acid di-chloride and 2-amino-1,3-propanediol in a solvent selected from the group consisting of a lower alcohol or monoalkyl ether glycol.

2. A process for the preparation of S-N,N'-bis[2-hydroxy-1-(hydroxymethyl)ethyl]-5-[(2-hydroxy-1-oxopropyl)amino]-2,4,6-triiodo-1,3-benzenedicarboxamide, said process comprising forming S-N,N'-bis[2-hydroxy-1-(hydroxymethyl)ethyl]-5-[(2-acetyloxy-1-oxopropyl)amino]-2,4,6-triiodo-1,3-benzenedicarboxamide from S-(−)-5-[[2-(acetyloxy)-1-oxopropyl]-amino]-2,4,6-triiodo-1,3-benzendicarboxylic acid di-chloride and 2-amino-1,3-propanediol in a solvent selected from the group consisting of a lower alcohol or monoalkyl ether glycol, wherein the minimum molar ratio of 2-amino-1,3-propanediol to S-(−)-5-[[2-(acetyloxy)-1-oxopropyl]amino]-2,4,6-triiodo-1,3-benzenedicarboxylic acid dichloride ranges from 6 to 25.

3. A process for the preparation of S-N,N'-bis[2-hydroxy-1-(hydroxymethyl)ethyl]-5-[(2-hydroxy-1-oxopropyl)amino]-2,4,6-triiodo-1,3-benzenedicarboxamide, said process comprising forming S-N,N'-bis[2-hydroxy-1-(hydroxymethyl)ethyl]-5-[(2-acetyloxy-1-oxopropyl)amino]-2,4,6-triiodo-1,3-benzenedicarboxamide from S-(−)-5-[[2-(acetyloxy)-1-oxopropyl]-amino]-2,4,6-triiodo-1,3-benzendicarboxylic acid di-chloride and 2-amino-1,3-propanediol in a solvent selected from the group consisting of a lower alcohol or monoalkyl ether glycol, wherein the minimum molar ratio of 2-amino-1,3-propanediol to S-(−)-5-[[2-(acetyloxy)-1-oxopropyl]amino]-2,4,6-triiodo-1,3-benzenedicarboxylic acid dichloride ranges from 8 to 15.

4. The process according to claim 1, 2 or 3, in which the solvent is a straight or branched $C_2$–$C_5$ alcohol.

5. The process according to claim 1, 2 or 3, in which the solvent is selected from the group consisting of $C_2$–$C_5$ secondary alcohols.

6. The process as claimed in claim 5, in which the solvent is selected from the group consisting of: isopropanol, sec-butanol and t-butanol.

7. The process according to claim 1, 2 or 3, in which the solvent is a $C_3$–$C_7$ glycol monoalkyl ether.

8. The process as claimed in claim 7, in which the solvent is selected from 2-methoxyethanol and 2-ethoxyethanol.

9. The process according to claim 1, 2 or 3, in which the reaction temperature for the preparation of S-N,N'-bis[2-hydroxy-1-(hydroxymethyl)ethyl]-5-[(2-acetyloxy-1-oxopropyl)amino]-2,4,6-triiodo-1,3-benzenedicarboxamide ranges from 48 to 85° C. and the reaction time ranges from 2 to 6 hours.

10. The process according to claim 1, 2, or 3, including an additional step at the end of the reaction between 2-amino-1,3-propanediol and S-N,N'-bis[2-hydroxy-1-(hydroxymethyl)ethyl]-5-[(2-acetyloxy-1-oxopropyl)amino]-2,4,6-triiodo-1,3-benzenedicarboxamide, of distilling off the solvent to dryness under pressure, hydrolyzing the acetate group by addition of water and heating the solution to 50–70° C., wherein the temperature is maintained for a time from 4 to 8 hours; thereafter neutralizing the solution by addition of hydrochloric acid, then concentrated and purified by elution on a macroporous highly cross-linked styrene resin and subsequently on a strong sulfonic type cationic resin, regenerated in the acidic form, and on a secondary amine-type mean anionic resin, regenerated in the OH⁻ form.

11. The process as claimed in claim 10, in which the acetate group is hydrolyzed at a temperature ranging from 55 to 65° C. for a time from 5 to 7 hours.

* * * * *